United States Patent

Pottgen et al.

[11] Patent Number: 5,524,618
[45] Date of Patent: Jun. 11, 1996

[54] METHOD AND APPARATUS FOR MEASURING HEAT FLOW

[76] Inventors: Paul A. Pottgen, 4561 Dogwood Dr., Allison Park, Pa. 15101; Neil J. Szuminsky, 1427 Hilsdale Ave., Pittsburgh, Pa. 15216

[21] Appl. No.: 70,185

[22] Filed: Jun. 2, 1993

[51] Int. Cl.$^6$ .................................................. A61B 5/00
[52] U.S. Cl. ............................. 128/633; 128/632; 128/736
[58] Field of Search ..................... 374/29; 128/632, 128/633, 664, 742, 746, 736; 482/8

[56] References Cited

U.S. PATENT DOCUMENTS

| | | | |
|---|---|---|---|
| 4,191,917 | 3/1980 | Benzinger | 128/736 |
| 4,345,844 | 8/1982 | Birukoff | |
| 4,364,398 | 12/1982 | Sassi et al. | 128/736 |
| 4,392,005 | 7/1983 | Mohrman | 128/736 X |
| 4,762,423 | 8/1988 | Basta | |
| 4,909,256 | 3/1990 | Peck | 128/632 |
| 4,957,108 | 9/1990 | Schoendorfer et al. | 128/632 |
| 5,040,541 | 8/1991 | Poppendiet | |
| 5,050,612 | 9/1991 | Matsumura | 128/736 X |
| 5,135,311 | 8/1992 | Alpert | |
| 5,267,563 | 12/1993 | Swedlow et al. | 128/664 X |
| 5,291,181 | 3/1994 | DePonte | 128/736 X |

FOREIGN PATENT DOCUMENTS

89/09566  10/1989  WIPO .................................... 128/664

*Primary Examiner*—Sam Rimell
*Attorney, Agent, or Firm*—Michael J. Kline; Darren E. Wolf; Carol I. Bordas

[57] ABSTRACT

Method and apparatus for determining caloric expenditure of a subject. The apparatus includes a modified heat flow sensor having an overlay and/or conductive layer for measuring the evaporative heat loss component, in addition to substantially total heat loss, for the subject.

17 Claims, 2 Drawing Sheets

METHOD AND APPARATUS FOR MEASURING HEAT FLOW

FIELD OF THE INVENTION

The present invention relates to a method and apparatus to measure convective, conductive, radiant, and evaporative heat flow. More specifically, in a preferred embodiment, the invention is used to estimate total heat loss from a human body or other living subject by measuring heat flow from several portions of the body, each of which is assumed to be representative of heat loss over that particular region of the body. From this measurement of total heat flow, a calculation of caloric expenditure can be made.

BACKGROUND AND PRIOR ART

The determination of caloric expenditure is an important component of any weight control or fitness program. The number of calories burned is generally estimated through the use of tabulated values for a given activity or by the use of workload measurements on exercise equipment such as treadmills or bikes. Neither, however, is particularly reliable. The tables are generally only average rates for a 70 kg individual performing each activity in some arbitrary, average manner. Certainly not very reflective of any given individual's caloric expenditures, the tables may vary as much as 50% from actual caloric expenditures. Exercise equipment having caloric calculators makes similar errors, and such equipment fails to provide any indication of total caloric expenditure for the day.

A more reliable approach would be to actually monitor the caloric expenditure. The body's metabolic "engines" generate significant amounts of heat; at rest this heat generation is equivalent to that of a 100 watt light bulb. In the human body's attempt to maintain a body temperature of 98.6° F., it controls heat loss to the environment by regulating blood flow to the body surface. At rest, blood flow to the skin is restricted and the surface of the skin may be as much as 20° F. cooler than the body core. This results in a lower flux of heat to the environment. With exercise however, the excess heat generated by physical exertion (approximately 80% of the energy needed to contract human muscles is wasted as heat) must be dumped to the environment to maintain constant body temperature. Blood flow is diverted to the skin, raising its temperature and the rate at which heat is dumped to the environment is increased.

As a homoiotherm, the body maintains a nearly constant internal body temperature by balancing the generation of heat by its metabolic process with controlled loss of heat through an orchestration of evaporative, convective, radiant, and conductive heat loss mechanisms. At rest in normal room temperature conditions, the body can utilize convective and radiant heat loss (with minor conductive heat loss contributions as well) to regulate body temperature, primarily by control of blood flow to the skin surfaces. If an individual is exercising or is in ambient temperatures above 35° C., the convective and radiant heat loss is inadequate to control internal temperature and the body begins to utilize evaporative heat loss. Evaporation, both that which occurs insensibly (i.e. without obvious sweating) and sensibly (i.e. with obvious sweating) can provide several fold greater heat loss than the other two mechanisms combined.

Heat flow can be accurately measured with a whole body calorimeter. This device is a chamber in which the subject is placed and the total heat given off by the subject's body can be captured and measured. The disadvantages of a whole body calorimeter are that it is expensive, relatively immobile, and the actions and motions of the subject are limited to the space within the chamber. See W. H. Close, M. J. Dauncey, and D. L. Ingram (1980), "Heat loss from humans measured with a direct calorimeter and heat-flow meters", Br. J. Nutr. 43, 87, pp 87-93.

In order to overcome the disadvantages of the whole body calorimeter, a sampling technique using heat flow sensors has been developed to estimate the total heat loss from a subject by measuring heat loss on only a few selected locations on the subject's skin surface. Each measured value is multiplied by a "weighting co-efficient" in order to estimate the heat loss for that particular region of the subject's body. The sum of all regional heat loss components is the estimate of the total heat loss. One system of "weighting co-efficients" has been developed by Hardy and DuBois. See Archives of Internal Medicine, Vol. 17, No. 6, pp. 863-871 (1916).

Traditional heat flow sensors are generally based on the measurement of the temperature differential that occurs across a material due to the thermal resistance of that material. In order for the sensor to accurately measure the heat flow, it must not add a significant insulating layer and it must lose heat from its surface in the same manner as the surface on which it is placed. The available heat flow sensors perform well on inanimate objects such as walls, doors, boilers, and pipes, where convective, radiant, and conductive heat loss mechanisms predominate. They are, however, inadequate for measuring heat loss from the human body, where evaporative heat loss may be significant.

Current heat flow sensors, such as that produced by RdF, are unable to reliably include the component of evaporative heat loss from the body as part of its output signal for two main reasons; 1) such sensors actually occlude the surface of the skin, preventing evaporation; therefore, any moisture that does move from under the sensor evaporates from the skin surface adjacent to the sensor and not from the sensor surface itself, and 2) when used to monitor body heat loss, these sensors actually show a decreased heat flow as the evaporative heat loss increases, thereby reducing the skin surface temperature.

Accordingly, a significant advance in the art could be realized if a heat flow sensor capable of measuring all components of heat loss, including evaporative heat loss, could be developed.

SUMMARY OF THE INVENTION

The present invention is a method and apparatus for determining caloric expenditure by measuring all components of heat flow. It is small, portable, relatively inexpensive, and can be worn on the subject's body with no significant limitation on motion or mobility. The present invention utilizes a modified heat flow sensor element that is superior to heat flow sensors currently used, which fail to measure evaporative heat loss. Currently, only devices such as whole body calorimeters are capable of measuring all components of heat loss. As previously stated, these devices are large, expensive, relatively immobile, and limit the activity of the subject.

In order to measure evaporative heat loss with a heat flow sensor element, the present invention covers the sensor element, which may otherwise be conventional, with an overlay material which allows the evaporating fluid to migrate from the monitored surface (i.e., skin) to the ambient air side of the heat flow sensor element and subsequently to evaporate from the surface of the heat flow sensor element. To further facilitate the measurement of evaporative heat loss, the preferred embodiment of the present invention creates a substantially uniform temperature over the ambient air surface of the heat flow sensor and the surrounding measured surface. In a highly preferred embodiment, this is accomplished using a thermally conductive layer which is placed over the ambient air surface of the heat flow sensor element and overlapped onto the measured surface.

DETAILED DESCRIPTION OF THE PREFERRED EMBODIMENTS

Although the present invention has many applications, the following discussion will focus on the sensing of caloric expenditure, for example, by measuring heat flow from a living being (human or animal) where the surface that is monitored is skin and the fluid through which the evaporative component of heat flow occurs is perspiration. This, however, is not the only application of the present invention. Other uses of the present invention include, for example optimization of evaporative coolers.

The present invention measures conductive, convective, radiant, and evaporative heat flow using a modified heat flow sensor element. Any heat flow sensor element satisfying the following parameters will be satisfactory for the present invention: small size, flexible, adequate sensitivity. Acceptable heat flow sensor elements can be obtained from RdF, Hudson, N. H., sold as the Micro-Foil™ Heat Flow Sensor. Any other heat flow sensor element meeting the requirements of the invention specified herein would be acceptable, including thermopile, thermistor, and thermocouple-based heat flow sensor elements.

Figure 1:
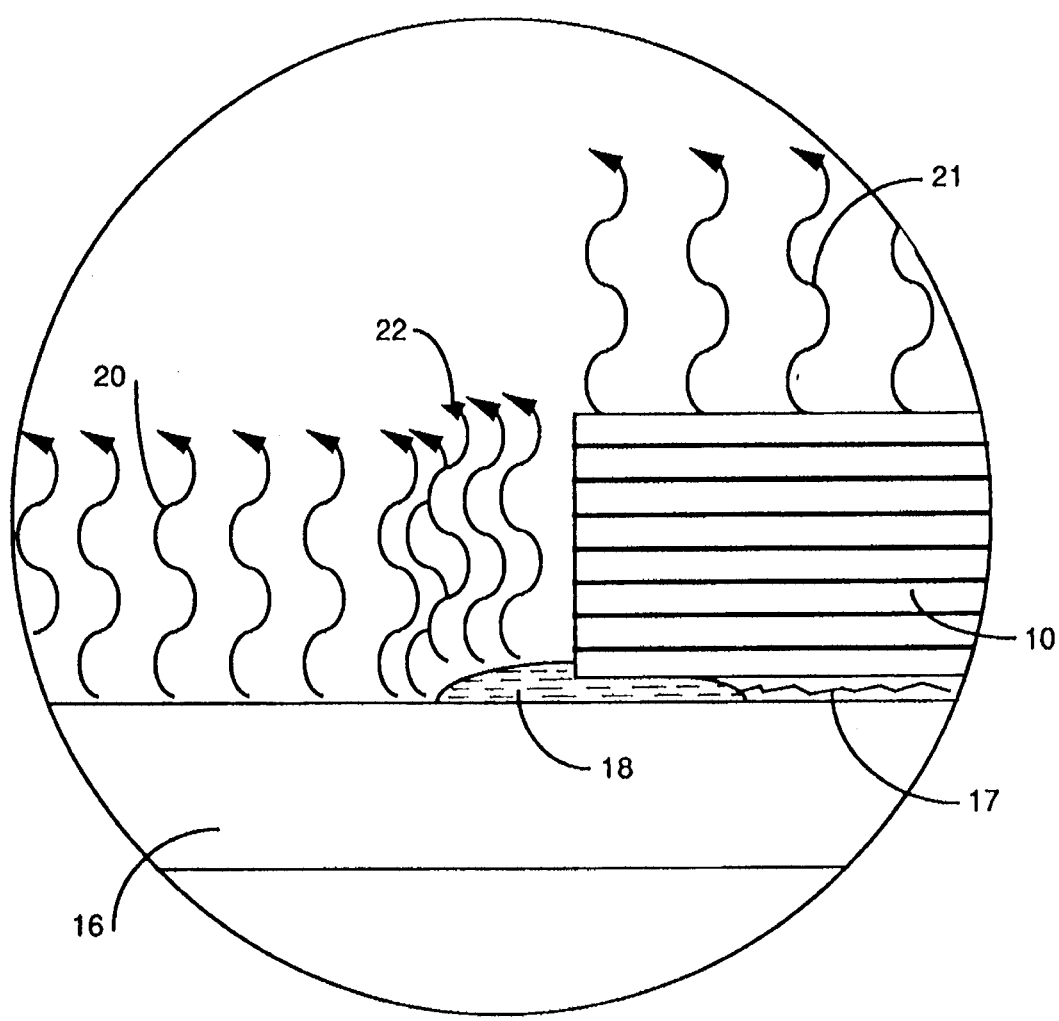
FIG. 1 is a cross-sectional view of a conventional heat flow sensor as presently used.

Evaporative heat loss occurs when perspiration on the skin surface evaporates. FIG. 1 is a cross-sectional view of a conventional heat flow sensor element as typically used. In this arrangement the heat flow sensor element 10 traps perspiration 17 against the subject's skin 16. This prevents the perspiration 17 from evaporating and prevents evaporative heat loss from the area of skin 16 covered with the heat flow sensor element 10. Since the heat flow sensor element 10 is not measuring evaporative heat flow, which is occurring on the surrounding skin 16, the heat flow measurement is not representative of the heat loss 20 on the surrounding skin 16. This error will cause the estimated heat loss 21 to be lower than the actual heat loss 20 by an amount equal to the heat loss due to evaporation. As a result of the heat flow sensor element 10 preventing the evaporation of perspiration under the sensor 17, perspiration 17 will accumulate under the sensor 10 and some perspiration will leak out, 18, and collect in the region surrounding the sensor 10. This collection of perspiration 18 around the edge of the heat flow sensor element 10 will cause an increased heat loss 22 in the region surrounding the sensor 10. Since conventional heat flow sensor elements 10 are most sensitive in the center of the sensor area and least sensitive at the fringe area, the increased heat loss 22 in the area surrounding the sensor 10 will not be detected.

Figure 2:
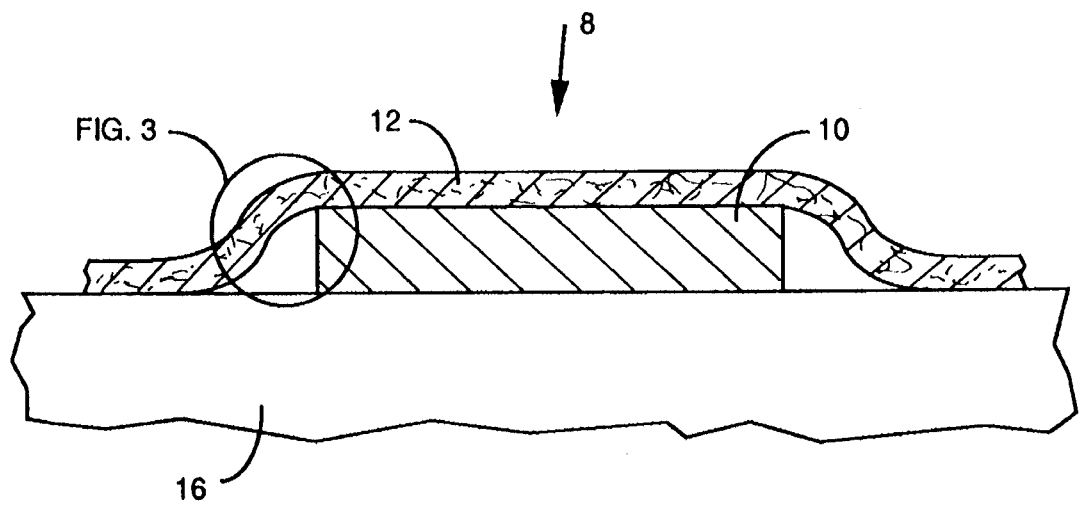
FIG. 2 is a cross-sectional view of a preferred embodiment of the present invention in use.
Figure 3:
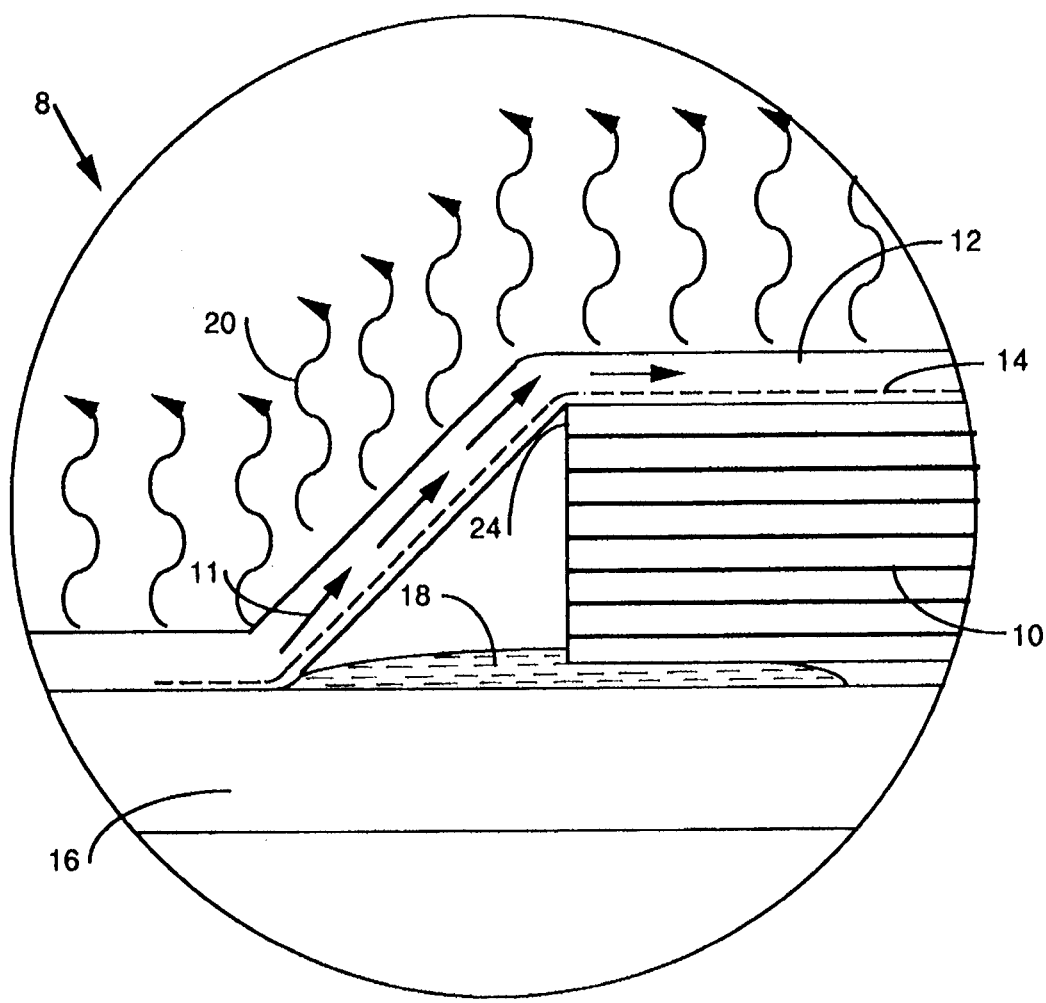
FIG. 3 is a closeup of the portion of FIG. 2 shown encircled.

The present invention minimizes and compensates for the shortcomings of conventional heat flow sensors element 10 so that evaporative heat flow can be measured. One embodiment of the present invention, generally, 8, is depicted in FIGS. 2 and 3. A heat flow sensor element 10 is positioned on a surface 16, such as skin, as will subsequently be described.

In order to induce evaporative heat loss on the ambient air side 24 of the heat flow sensor element 10, the present invention provides an overlay material 12 which allows the perspiration build-up 18 around the fringe of the heat flow sensor element 10 to migrate through the overlay material 12 as illustrated by the arrows 11, to the ambient air side 24 of the heat flow sensor 10. This migration allows perspiration to evaporate from the outer surface 24 of the heat flow element 10, which simulates the evaporative heat loss which is occurring on the subject's skin surface 16. In the preferred embodiment of the invention, the overlay material 12 has a perspiration evaporation rate similar to that of the skin of the subject 16 under the same conditions. This evaporation rate typically can vary as much as and is preferably within the range of 20 $g/m^2/day$ to 100 $g/m^2/hr$.

The overlay material 12 should be capable of "imbibing" evaporative fluid, such as perspiration, preferably "wicking" the perspiration from the skin surface 16 to the ambient air side 24 of the heat flow sensor element 10. Overlay materials which appear to function best are constructed of leather, synthetic membranes, tight weave fabric, etc. An example of a synthetic membrane suitable as an overlay material is manufactured by Millipore. Other examples of suitable synthetic membranes include those sold under the trade names Thermipor, and Versapor™ manufactured by Gelman Sciences, Inc., Ann Arbor, Mich.

In general, the thinner the overlay material 12 is, the better the process of the invention works. Additionally, it has been found that overlay materials having 1 micron openings are particularly well-suited to "wicking" the perspiration build-up 18 from the measured surface 16 to the ambient air side 24 of the heat flow sensor element 10. An example of suitable tight weave material is Spectra/Mesh, manufactured by Spectrum of Los Angeles, Calif.

To further reduce measurement error, the preferred embodiment includes a thermally conductive layer 14 placed across both the ambient air side 24 of the sensor element 10 and a portion of the surrounding skin surface 16. This creates a substantially uniform heat flow across both the skin surface 16 and the top 24 of the heat flow sensor element 10 so that the top surface 24 of the heat flow sensor element 10 will sense substantially the same heat flow 20 as is occurring across the surrounding skin surface 16. This helps to correct heat flow variation caused by less perspiration, and thus less evaporation, on the top 24 of the heat flow sensor element 10 than on the skin surface 16. In the preferred embodiment of the invention, the thermally conductive material is selected from the group consisting of metal foil, including, by way of example but not limitation, copper, aluminum, stainless steel, and gold foils, vacuum deposited metal film, and thermally conductive plastics, and preferably has a thickness ranging from about 3000 Å to 2 mils.

Although the preferred embodiment of the present invention contains both an overlay material and a thermally conductive layer, the present invention also includes the use of either element alone.

In order to prevent artificial heat retention in the tissue surrounding the heat flow sensor 8, the method of fastening the apparatus to the user should not inhibit heat flow. If the method of fastening the apparatus to the user traps heat against the skin surface, there is a danger that the artificially increased skin temperature will cause a measurement error by the heat flow sensor. A preferred embodiment of the invention, therefore, uses an open weave material, preferably having openings of ⅛–¼ inch and over 95% open area, to fasten the device to the user; however, other materials may also be used.

In a highly preferred method of practicing the invention, multiple heat flow sensors 8 each having overlays 12 and/or thermally conductive layers 14 are positioned at various locations on the subject's body, to determine a total heat loss value for the subject. In another highly preferred embodiment of the invention, a single heat flow sensing apparatus 8 is placed at a location on the subject's body that is typical of heat loss for that subject. Such typical regions may vary from subject to subject, and may be determined by applying multiple sensing apparatus 8 to the subject, evaluating each sensor individually and identifying the sensor or sensors that most nearly represent the total heat loss for all sensors for that subject. Once a "typical" region for heat loss is identified for that subject, the subject need only use one sensor 8 attached to that typical region.

In a most highly preferred embodiment of the invention, the sensing apparatus 8 is attached to the wearer with, for example, an elastic armband which may be fabricated of an open weave material that allows the wearer to exercise freely. The heat flow information may be continuously monitored and recorded by a microcontroller or analog device capable of converting heat flow information into caloric expenditure information, both in terms of rate of caloric expenditure and cumulative caloric expenditure. Such microcontrollers include, by way of example, those available from Intel, including the Intel 8051 family.

Caloric expenditure may be calculated in a number of ways from the measure of heat flow obtained from the methods and apparatus of the present invention. A preferred method is based on the following equation:

Caloric expenditure (k-cal)=total body surface area (m$^2$)× fraction of body surface sampled by each sensor (1 for one sensor sensing typical region of heat flow)×heat flux (k-cal/m$^2$/min.)×time of sensing (min.)

The microcontroller is preferably programmed to continually monitor, record, and total heat flux for the subject, thereby allowing both an instantaneous rate of caloric expenditure and a total caloric expenditure for the subject to be monitored.

Figure 4:
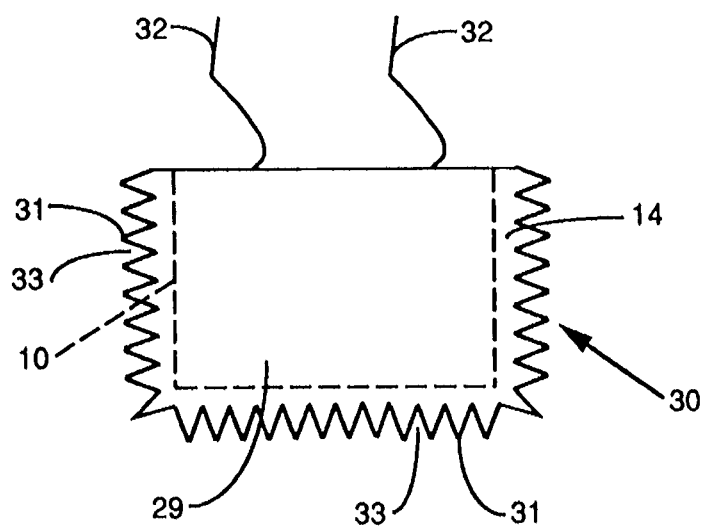
FIG. 4 is a schematic plan view of a preferred sensor for measuring heat loss of the invention.

As illustrated in FIG. 4, in a highly preferred embodiment of the invention, the thermally conductive layer 14 may include center surface area 29 and a fringe region, generally 30, extending beyond the perimeter of the sensor element 10. This fringe region 30 may comprise a series of "fingers" 31 formed in the thermally conductive layer 14. The fringe area 30 preferably is located about a substantial portion of the periphery of the heat flow sensor element 10, but may exclude that portion through which the wire connectors 32 of the heat flow sensor element 10 pass. As illustrated, the fingers 31 have an open area 33 between adjacent fingers.

Although the invention has been described in detail with reference to specific examples and preferred embodiments, it is to be understood that the full scope of the invention is defined by the following claims, as properly interpreted, including all equivalents thereof.

What is claimed is:

1. An apparatus for determining caloric expenditure by measuring total heat flow from the skin surface of a wearer of said apparatus, comprising:

(a) heat flow sensor means for measuring convective, conductive, radiant and evaporative heat flow; and (b) an overlay material, at least a portion of which contacts said wearer's skin surface and another portion of which covers said heat flow sensor means, said overlay material being capable of imbibing a fluid and allowing said fluid to migrate from said skin surface to the portion of said overlay material contacting said heat flow sensor means such that said imbibed fluid can evaporate from said portion of said overlay material covering said heat flow sensor means.

2. The apparatus of claim 1 wherein said skin surface and said overlay material have essentially the same evaporation rate.

3. The apparatus of claim 2, wherein said evaporation rate is within the range of 20 g/m$^2$/day to 100 g/m$^2$/hr.

4. The apparatus of claim 1, wherein said overlay material is selected from the group consisting of leather, synthetic membranes, and tight-weave fabrics.

5. The apparatus of claim 1, including a fastening means for attaching said apparatus to said wearer.

6. The apparatus of claim 5 wherein said fastening means comprises an open weave material.

7. An apparatus for measuring heat flow from a surface on which said apparatus is placed comprising:

(a) heat flow sensor means;

(b) an overlay material, at least a portion of which contacts said heat flow sensor means on a surface of said heat flow sensor means exposed to ambient air, said overlay material being capable of imbibing a fluid and allowing said fluid to migrate from said surface on which said apparatus is placed to the portion of said overlay material contacting said heat flow sensor and evaporate therefrom; and (c) a thermally conductive material located between said heat flow sensor and said overlay material to create a substantially uniform heat flow across said surface of said heat flow sensor means.

8. The apparatus of claim 7, wherein said thermally conductive material is selected from the group consisting of metal foil, vacuum deposited metal film, and thermally conductive plastics.

9. The apparatus of claim 8, wherein both said overlay material and said skin have essentially the same evaporation rate.

10. The apparatus of claim 9, wherein said evaporation rate is within the range of 20 g/m$^2$/day to 100 g/m$^2$/hr.

11. The apparatus of claim 8, wherein said heat flow sensor means is selected from the group consisting of thermopile, thermistor and thermocouple-based heat flow sensors.

12. The apparatus of claim 8, wherein said overlay material is selected from the group consisting of leather, synthetic membranes, and tight weave fabrics.

13. The apparatus of claim 8, including a fastening means to attach said apparatus to said surface.

14. The apparatus of claim 13, wherein said fastening means consists of an open weave material.

15. The apparatus of claim 7, wherein both said overlay material and said thermally conductive material extend beyond at least one edge of said heat flow sensor means to said surface on which said apparatus is placed.

16. The apparatus of claim 7 further including microcontroller means for converting heat flux data obtained from said heat flow sensor means into caloric expenditure data.

17. The apparatus of claim 15 wherein said thermally conductive material comprises a plurality of adjacent projections having a space therebetween said projections extending beyond said heat flow sensor means and contacting said surface on which said apparatus is placed.

* * * * *